United States Patent
Grozelier

(10) Patent No.: US 11,571,163 B2
(45) Date of Patent: Feb. 7, 2023

(54) SURFACE CUTTING DEVICE, IN PARTICULAR FOR ALLERGY DIAGNOSIS

(71) Applicant: A2M, Saint Mesmin (FR)

(72) Inventor: Isabelle Grozelier, Saint Mesmin (FR)

(73) Assignee: A2M

( * ) Notice: Subject to any disclaimer, the term of this patent is extended or adjusted under 35 U.S.C. 154(b) by 512 days.

(21) Appl. No.: 16/637,500

(22) PCT Filed: Aug. 7, 2018

(86) PCT No.: PCT/EP2018/071426
§ 371 (c)(1),
(2) Date: Feb. 7, 2020

(87) PCT Pub. No.: WO2019/030238
PCT Pub. Date: Feb. 14, 2019

(65) Prior Publication Data
US 2020/0221992 A1 Jul. 16, 2020

(30) Foreign Application Priority Data

Aug. 8, 2017 (FR) ...................................... 1757581

(51) Int. Cl.
*A61B 17/3209* (2006.01)
*A61B 5/00* (2006.01)
(Continued)

(52) U.S. Cl.
CPC ............ *A61B 5/411* (2013.01); *A61B 17/205* (2013.01); *A61B 17/32093* (2013.01);
(Continued)

(58) Field of Classification Search
CPC ...... A61B 2017/320004; A61B 17/205; A61B 17/32093; A61B 17/3468; A61B 5/411;
(Continued)

(56) References Cited

U.S. PATENT DOCUMENTS

| 2,522,309 A | 9/1950 | Frank |
| 3,136,314 A | 6/1964 | Kravitz |

(Continued)

FOREIGN PATENT DOCUMENTS

| FR | 1292190 A | 4/1962 |
| FR | 1309352 A | 11/1962 |

(Continued)

OTHER PUBLICATIONS

International Search Report from Application No. PCT/EP2018/071426 dated Nov. 15, 2018, 2 pages.

*Primary Examiner* — Deanna K Hall
(74) *Attorney, Agent, or Firm* — Lerner, David, Littenberg, Krumholz & Mentlik, LLP

(57) ABSTRACT

The present invention relates to a cutting device comprising a manual gripping element (100) and a cutting assembly (200) that is positioned on one end of the gripping element (100) and comprises a punch (210) split into at least two cutting tips (220, 230), at least one of these tips (220, 230) being hinged on the gripping element (100) in order to be movable between a rest and cutting position in which the tips (220, 230) are adjacent and a working and injection position in which the tips (220, 230) are spaced apart, and urging means (250) designed to move each movable tip (220, 230) into the working position when these urging means (250) press against the skin.

14 Claims, 9 Drawing Sheets

Figure 1:
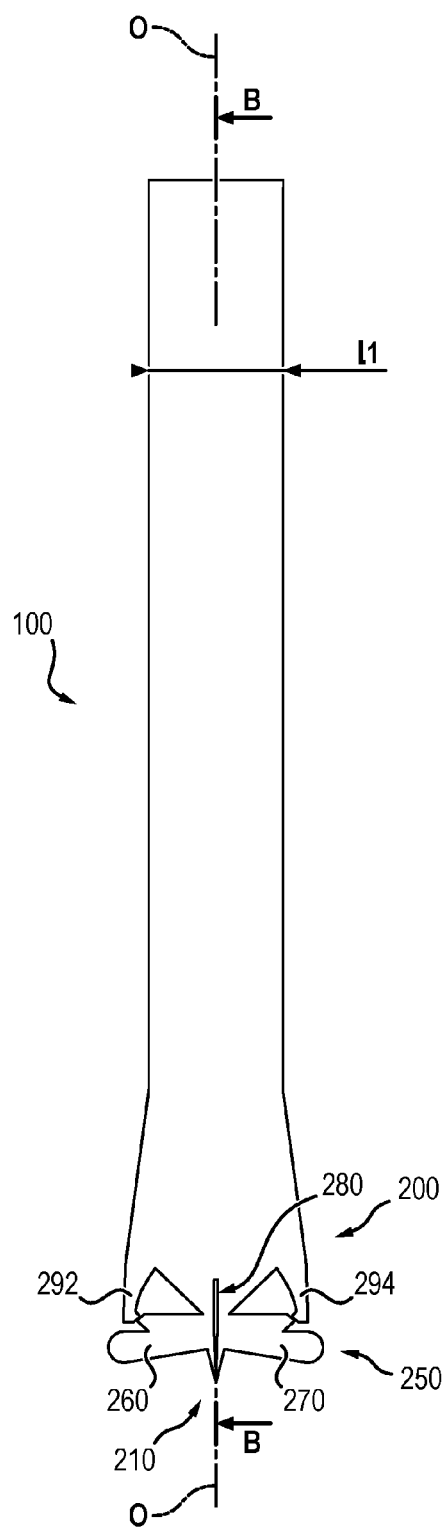

(51) Int. Cl.
*A61B 17/20* (2006.01)
*A61B 17/34* (2006.01)
*A61B 17/00* (2006.01)
*A61M 37/00* (2006.01)

(52) U.S. Cl.
CPC ............... *A61B 17/3468* (2013.01); *A61B 2017/00747* (2013.01); *A61M 2037/003* (2013.01); *A61M 2037/0023* (2013.01)

(58) Field of Classification Search
CPC ............ A61B 2017/00747; A61M 2037/0023; A61M 2037/003
See application file for complete search history.

(56) References Cited

U.S. PATENT DOCUMENTS

| | | |
|---|---|---|
| 3,194,237 A | 7/1965 | Rubin |
| 3,221,739 A | 12/1965 | Rosenthal |
| 3,291,129 A | 12/1966 | Burelle et al. |
| 3,596,660 A | 8/1971 | Melone |
| 3,675,766 A | 7/1972 | Rosenthal |
| 4,453,926 A | 6/1984 | Galy |
| 4,583,982 A | 4/1986 | Vlock |
| 2007/0016100 A1 | 1/2007 | Miller |
| 2016/0256636 A1 | 9/2016 | Scherkowski |

FOREIGN PATENT DOCUMENTS

| | | |
|---|---|---|
| FR | 1349909 A | 1/1964 |
| FR | 2119120 A5 | 8/1972 |
| FR | 2474856 A1 | 8/1981 |
| FR | 2535602 A1 | 5/1984 |
| FR | 2748647 A1 | 11/1997 |

SURFACE CUTTING DEVICE, IN PARTICULAR FOR ALLERGY DIAGNOSIS

CROSS-REFERENCE TO RELATED APPLICATIONS

The present application is a national phase entry under 35 U.S.C § 371 of International Application No. PCT/EP2018/071426 filed Aug. 7, 2018, which claims priority from French Application No. 1757581 filed Aug. 8, 2017, all of which are hereby incorporated herein by reference.

TECHNICAL FIELD

The present invention relates to the field of devices for the superficial cutting of the skin of a patient, particularly for accomplishing an allergic diagnostic.

Cutaneous allergic diagnostic tests are generally called "prick tests".

PRIOR ART

Allergic diagnostic tests are medical tests consisting of causing a few microscopic drops of a product (an allergen for example) to superficially penetrate into the upper portion of the epidermis of a patient, for example on his forearm, in order to test the reactivity of this patient to said product.

In practice, after depositing a drop of product on the skin, the skin is pricked through the drop with a point, to cause the product to penetrate under the skin, then wait fifteen to twenty minutes before interpreting the cutaneous reaction.

Several systems now exist on the market to practice pricking the skin to ensure the penetration of the product under the skin. The general structure of known systems is always the same: a small plastic or metal stick is equipped with one, or possibly two or more, cutting point(s) at its end.

In particular, examples of such known devices will be found in documents FR 1292190, FR 1309352, FR 1349909, FR 2119120, FR 2474856, FR 2535602 and FR 2748647, as well as in documents U.S. Pat. Nos. 2,522,309, 3,136,314, 3,221,739, 3,596,660, 3,675,766, US 2016/256636, US 2007/016100, U.S. Pat. Nos. 3,194,237 and 4,583,982.

Set Problem

Devices proposed to date have already served well. However, they have not given total satisfaction.

In particular, currently known systems do not guarantee that they can cause an optimal and reproducible quantity of product to penetrate into the epidermis and false negative reactions exist for this reason without truly being identified.

Moreover, the useful quantity of product consumed for the accomplishment of each incision, and therefore each test, is much greater than that which is necessary.

Currently available cutting points also require an accurate and reproducible movement. An excessive pressure from the operator can in fact cause bleeding or a false positive result. Conversely, too low pressure can cause a false negative test.

Moreover, current use of a large majority of the known cutting points involves contact of the product distributor with the skin, the remaining product in the distributor then being used for other patients which potentially involves a risk of contamination between the different patients.

BASIS OF THE INVENTION

The main purpose of the invention is thus to propose a cutting device that is improved relative to the prior art.

One aim of the invention is in particular to propose an improved point suited for introducing some product in controlled volume into the epidermis, and to an accurately and reproducibly controlled depth, with a simple movement.

Another aim of the invention is to propose an economical cutting device which guarantees, without requiring special precautions, an incision that is strictly limited to the minimum necessary to optimize an allergic diagnostic test.

The aforementioned aims are achieved within the scope of the invention by means of a cutting device comprising:
- a manual gripping element and
- a cutting assembly located on one end of the gripping device and comprising a punch split into at least two cutting points, characterized in that one at least of these points is hinged on the gripping element in order to be movable between a resting and cutting position wherein the points are adjacent and a working and injection position wherein the points are separated, and that the device comprises urging means suited for moving each movable point into the working position when these urging means come to bear on the skin.

DETAILED DESCRIPTION OF THE FIGURES

Figure 2:
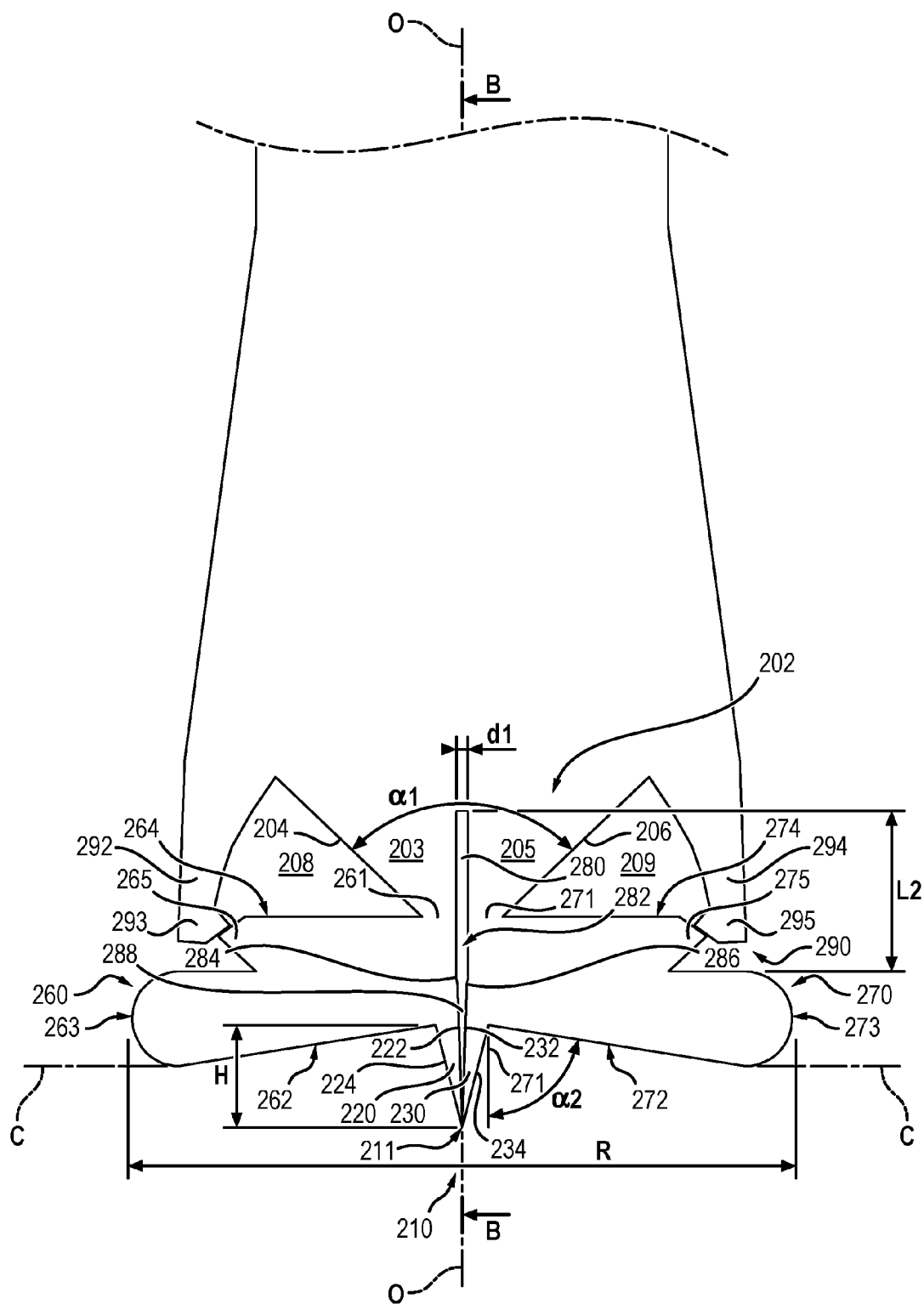
Figure 3:
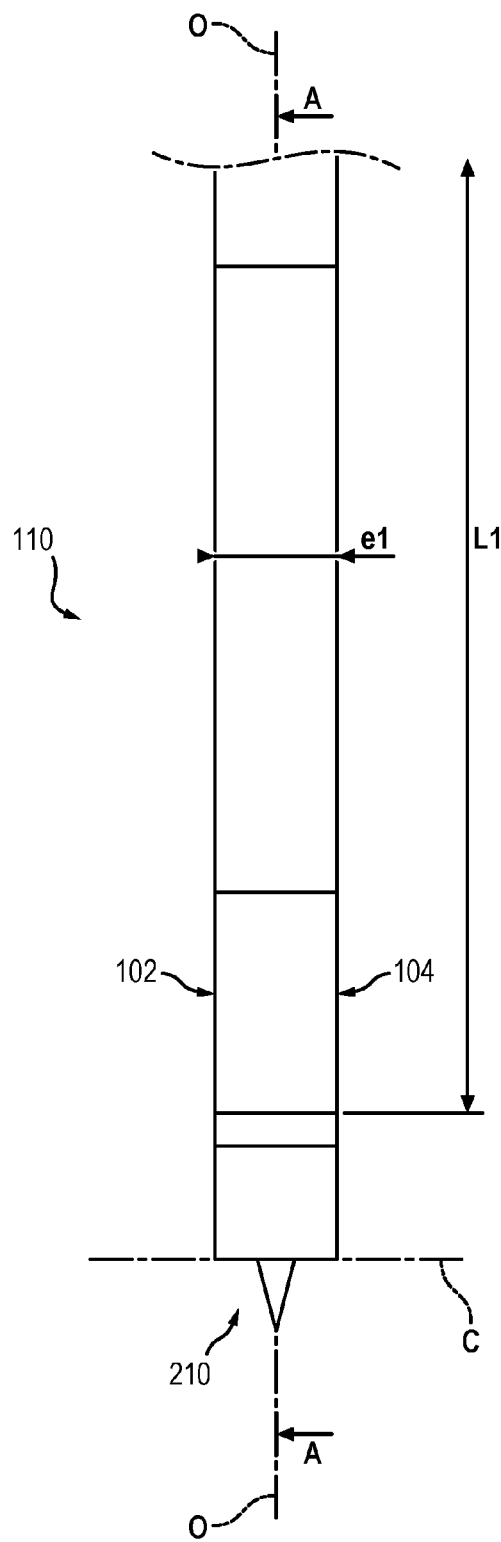
Figure 6:
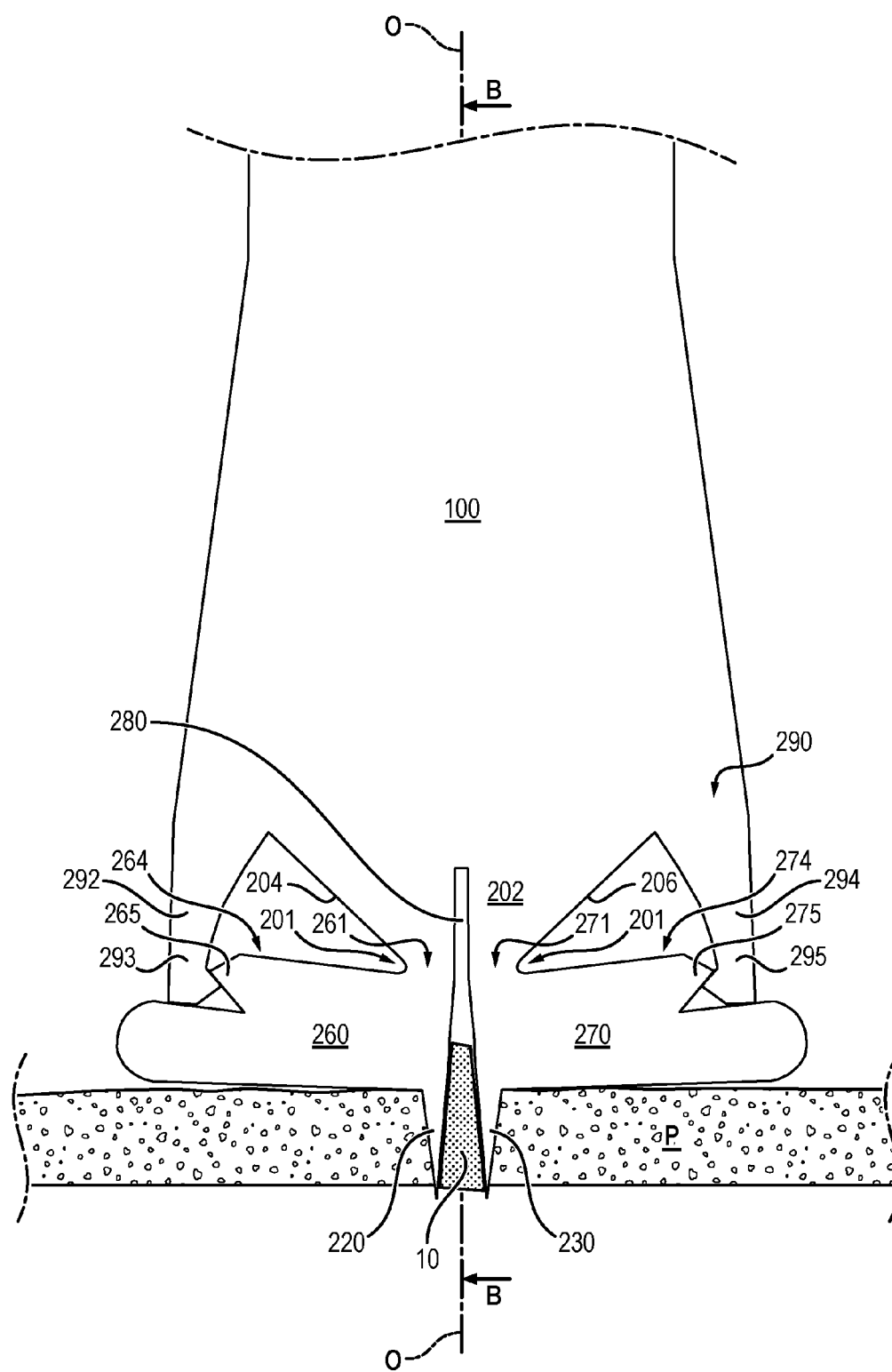
Figure 7:
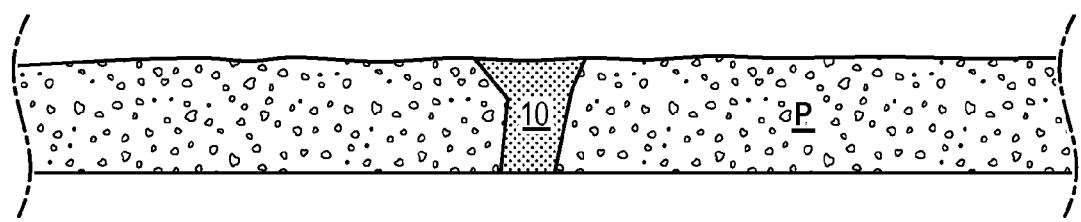
Figure 8:
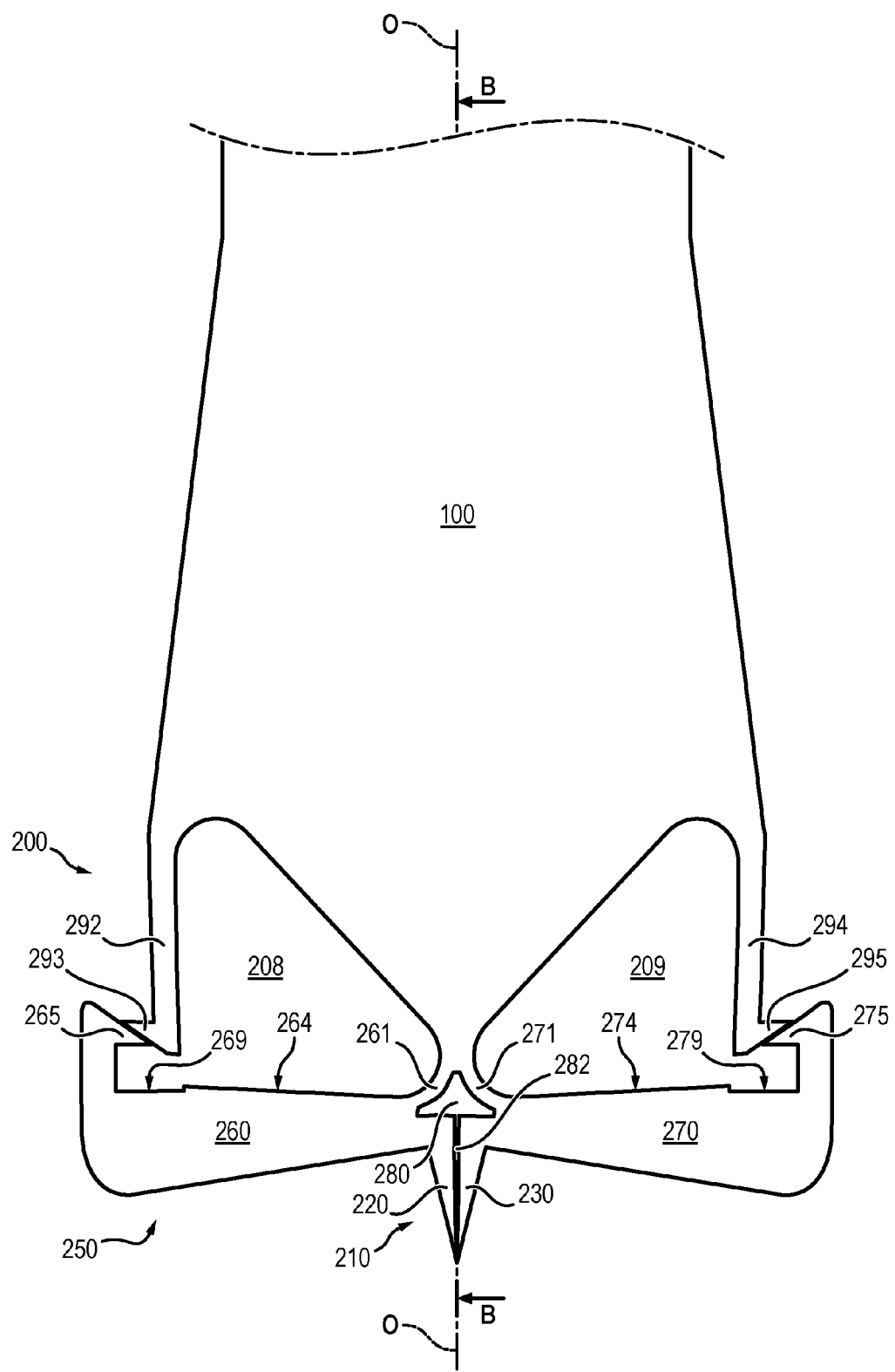
Figure 9:
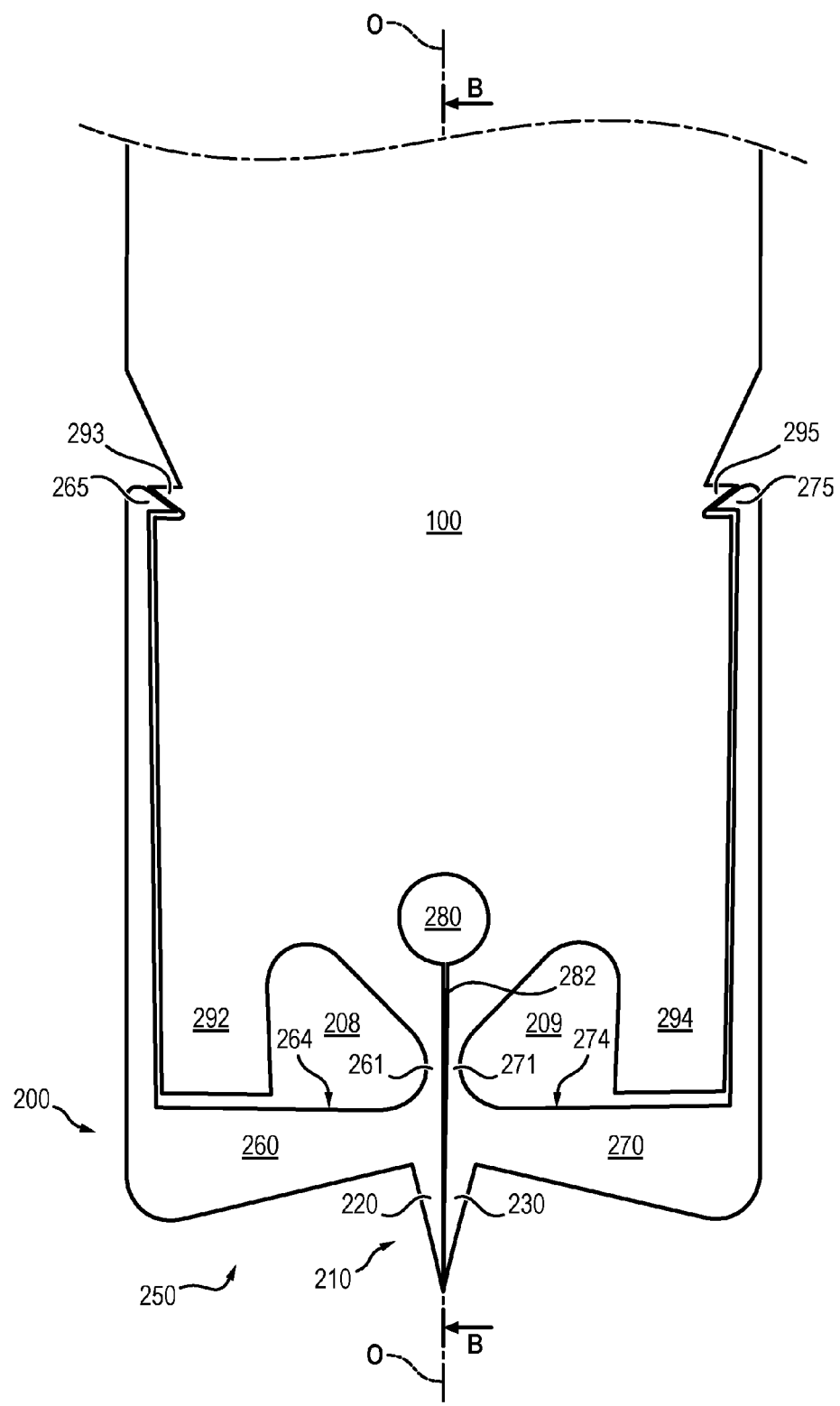

Other features, aims and advantages of the invention will appear upon reading the detailed description which follows, and referring to the appended drawings given by way of non-limiting examples, in which:

FIG. 1 represents a first side overview of a cutting device according to the present invention, FIG. 2 represents a partial detail view at enlarged scale of the end of a cutting device according to the invention, FIG. 3 represents a second side overview of a cutting device according to the invention at a viewing angle orthogonal to FIG. 1, FIGS. 4, 5 and 6 represent the same device according to the invention at three successive use steps for a cutaneous incision, FIG. 7 represents schematically a section view of the epidermis in which an injection has been accomplished by means of a cutting device according to the invention, and FIGS. 8 and 9 represent two side views similar to FIG. 1 of variants of a device according to the present invention.

DETAILED DESCRIPTION OF THE INVENTION

As previously indicated, and as can be seen in FIGS. 1, 2 and 3, the superficial cutting device according to the present invention comprises an elongated manual gripping element 100 and a cutting assembly 200 located on one end of the gripping element 100.

The cutting assembly 200 includes a punch 210 and urging means 250.

The punch 210 is split into at least two cutting points or needles 220, 230. One at least of these two points 220, 230 is hinged on the gripping element 100 in order to be movable between a resting and cutting position illustrated in FIGS. 1, 2 and 4 and a working and injection position illustrated in FIGS. 5 and 6.

In the resting position, the two points 220, 230 are adjacent and ready for an incision at a virtually unique point.

In the working and injection position, after having superficially penetrated the skin, the two points 220, 230 are separated.

The urging means 250 are suited for moving the movable point 220 and/or 230 into the working position when they come to bear on the skin of an individual.

The device according to the invention preferably has a longitudinal axis of symmetry O-O. More precisely still, the cutting device according to the invention preferably has two symmetry planes A-A and B-B shown in particular in FIGS. 1 and 3, secant to the axis O-O.

The side view of FIG. 1 is parallel to the symmetry plane A-A and orthogonal to the symmetry plane B-B. For its part, the view illustrated in FIG. 3 is parallel to the symmetry plane B-B and orthogonal to the symmetry plane A-A.

Within the scope of the invention, the punch 210 is preferably split into two cutting points 220, 230, and in this preferred embodiment each of the two points is hinged with rotation on the gripping element 100 between the resting and cutting position wherein the two points are adjacent and the working and injection position wherein the two points are separated, by rotation around a respective axis orthogonal to the plane A-A and parallel to the plane B-B.

The manual gripping element 100 can be the object of numerous embodiments.

Preferably, the manual gripping element 100 is formed of an elongated sleeve centered on the axis O-O.

The geometry of the cross section of the manual gripping element 100, in a plane orthogonal to the axis O-O, can also be the object of numerous variant embodiments.

This cross section can for example be a circle of revolution about the axis O-O or have the shape of a polygon, particularly a quadrilateral, for example rectangular or square.

The manual gripping element 100 can have for example, without this being a limitation, a minimal length L1 along the axis O-O about 45 mm, and a rectangular cross section having a width 11 in the A-A plane, and therefore orthogonally to the B-B plane, comprised between 4 and 15 mm and a thickness e1 in the plane B-B and therefore orthogonally to the plane A-A comprised between 0.2 (if made of metal for example) and 5 mm.

As can be seen in the appended figures, the end of each manual gripping element 100 which bears the cutting assembly 200 preferably has a tapered shape, for example in the form of a cone 202 convex toward the outside of the device, or a corner of an octahedron. The apex angle α1 of the cone 202 is typically about 90°.

The urging means 250 preferably have two strips 260, 270 diametrically opposed relative to the plane B-B. The strips 260, 270 preferably form a single piece in the vicinity of the point of the cone 202. The strips 260, 270 each extend in a direction orthogonal to the longitudinal axis O-O and more precisely to the plane B-B. The geometry of the shape of the urging means 250 can be optimized for improving its function of bearing on the skin, for example by widening it at its end.

As will be seen subsequently, the cone 202 is provided with an axial slot 282 in the plane A-A, intended to form a product reservoir 280.

Within the scope of the illustrative schematics, the two strips 260, 270 are thus hinged at the apexes of the two segments 203, 205 of the cone 202 located on either side of the slot 282. In the appended figures, the pivoting zones of the strips 260, 270 on the segments 203, 205 of the cone 202 are labeled 261, 271.

The apex of the two segments 203, 205 can be rounded off to distribute the bending load and thus avoid rupture of the selected material.

More precisely, as was illustrated as a variant in FIG. 6, the transition zones labeled 201 between the outer surfaces 204, 206 of the segments 203, 205 and the facing surfaces 264 and 274 of the strips 260 and 270 is preferably rounded off and not angular with a sharp angle to avoid rupture of the material at this point.

These pivoting zones 261, 271 form mean pivot axes which extend perpendicular to the plane A-A.

The axially outer surfaces 262, 272 of the strips 260, 270, located opposite to the gripping element 100, at rest, move away from the gripping element 100 in radially outward direction.

These surfaces 262, 272 are preferably flat.

In other words, the surfaces 262, 272 of the strips 260, 270 intended to come into contact with the skin of the patient form a concave dihedral in the direction of the skin, when the device is presented facing the epidermis, the cutting assembly 20 being directed toward the skin.

The angle α2 formed between the surfaces 262, 272 and the symmetry plane B-B is typically from 70 to 88°. The angle is selected in such a manner that the ends of the surfaces 262, 272 come into contact with the skin after the ends of the points have penetrated the surface of the epidermis, typically after the punch 210 has penetrated by approximately one third into the epidermis of the patient.

To this end, typically, the end 211 of the punch 210 extends beyond, by approximately two thirds of the axial height H of the punch relative to the radial plane C-C containing the radially external edges of the strips 260, 270 most distant axially from the gripping element 100.

The radially external contour 263, 273 of the strips 260, 270 is preferably rounded off as can be seen in the figures.

The axially inner surfaces 264, 274 of the strips 260, 270, located toward the gripping element 100 are preferably flat and, at rest, extend perpendicular to the plane B-B.

Thus are formed between these axially inner surfaces 264, 274 strips 260, 270, and the facing surfaces 204, 206 of the segments 203, 205 of the cone 202, spaces 208, 209 which allow movement in rotation of the strips 260, 270 toward the gripping element 100, when these strips 260, 270 are moved from the resting position to the working position. These spaces 208, 209 are preferably in the form of dihedrals diverging in radially outward direction.

The two strips 260, 270 also carry, centered on the axis A-A, the punch 210, more precisely the two points 220, 230 forming the punch.

The two points 220, 230 extend in axially outward direction. They are diametrically opposed relative to the plane B-B and preferably form a single piece respectively on the radially inner portion of the axially outer surfaces 262, 272 of the strips 260, 270 intended to come into contact with the skin of the patient.

The points 220, 230 are individualized by the extension of the slot 282 which leads axially to the outside of the device. At rest, their ends are however adjacent, and join at the axis O-O in the form of a sharpened cutting spike 211.

Each of the points 220, 230 preferably has the shape of a half cone and is preferably delimited by a radially inner surface 222, 232, flat and substantially parallel to the plane B-B, and an outer surface 224, 234, frustoconical or polyhedral. The inner surfaces 222, 232 form a dihedral diverging in the direction of the gripping element 10. The conical exterior surfaces 224, 234 form in combination a cone centered on the axis A-A, the base of which is located on the side of the gripping element 100 and the point 211 located opposite this gripping element 100 on the end of the device.

As previously indicated, a reservoir 280 delimited by a slot 282 is formed at the cone 202 between the two strips 260, 270 and the points 220, 230.

Preferably, the slot 282 leads laterally to the cone 202, i.e. on each of the flanks 102, 104 of the gripping element 100 parallel to the symmetry plane A-A.

The slot 282 delimits a chamber, forming a product reservoir, which extends longitudinally along the axis O-O. The slot 282 is preferably delimited by two mutually parallel faces 284, 286, parallel to the axis O-O and parallel to the symmetry plane B-B. The chamber 280 thus preferably has a parallelepiped contour on its upper portion.

The distance d1 between the two faces 284, 286 is preferably comprised between 0.02 and 0.8 mm, advantageously between 0.05 and 0.4 mm. The length L2 of the chamber 280 formed by the slot 282 in the cone and the strips 260, 270, is preferably comprised between 22 and 10 mm, advantageously between 2 and 6 mm.

The parallelepiped chamber 280 delimited by the faces 284, 286 is continued by a tapered channel 288, delimited by the aforementioned surfaces 222, 232 and which converge progressively in the direction of the point 211.

By way of a non-limiting example, the volume of the reservoir 280 is advantageously of the order of 0.2 µl, or comprised between 0.2 µl and 0.5 µl.

Moreover, the cutting device according to the present invention preferably has means 290 for locking the strips 260, 270 and the points 220, 230 in the working position, once this is reached.

To this end, preferably, as can be seen in the appended figures, the cutting device according to the invention comprises, on the exterior of the cone 202, two arms 292, 294 diametrically opposed relative to the plane B-B, extending in axially outward direction of the device and each provided at its end with a hook or lug 293, 295 directed to radially inward direction, i.e. toward the symmetry plane B-B.

The strips 260, 270 are provided with a structure of complementary hooks or lugs 265, 275, directed to radially outward direction.

These hood structures 265, 275 are formed by undercuts on a transition zone between the axially inner faces 264, 274 and the radially external contour 263, 273 of the strips 260, 270. At rest, the hook structures 265, 275 are axially outside the hooks 293, 295 provided on the arms 292, 294, while preferably being adjacent to them.

The radially outer diameter of the hooks 265, 275 provided on the strips 260, 270 is slightly greater than the radially inner diameter of the hooks 293, 295 provided on the arms 292, 294.

Thus, during movement of the strips 260, 270 from the resting position to the working position, the hooks 265, 275 urge the hooks 293, 295 in radial movement toward the exterior by elastic deformation of the arms 292, 294. Once the hooks 293, 295 have passed over the hooks 265, 275, the hooks 293, 295 elastically resume their initial position and retain the hooks 265, 275, as well as consequently the strips 260, 270 and the points 220, 230 in the working position as illustrated in FIG. 6.

The axial height H of the points 220, 230, which corresponds to the cutting depth, is typically comprised between 0.5 and 5 mm.

The radial bulk R of the strips 220, 230, which corresponds to the sum of the radial extent of the two strips 220 and 230, is typically comprised between 4 and 15 mm. This radial bulk R can easily be adapted, depending on the resistance of the hinge zones 261 and 271, to define an acceptable skin load. To this end, it is possible to provide strips with a greater radial dimension, perpendicular to the plane B-B.

To use the system according to the present invention, the procedure is as follows.

Figure 4:
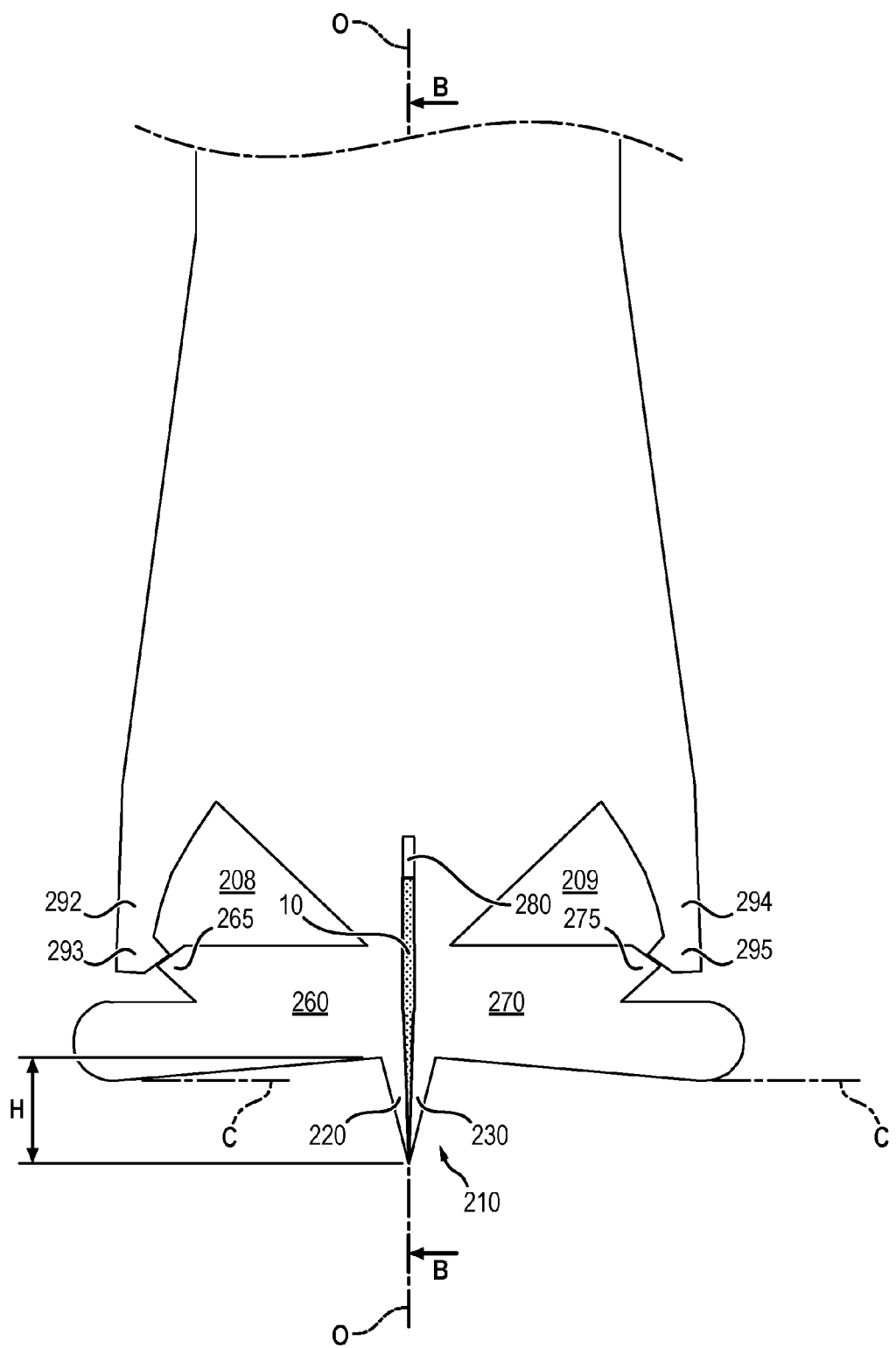
Figure 5:
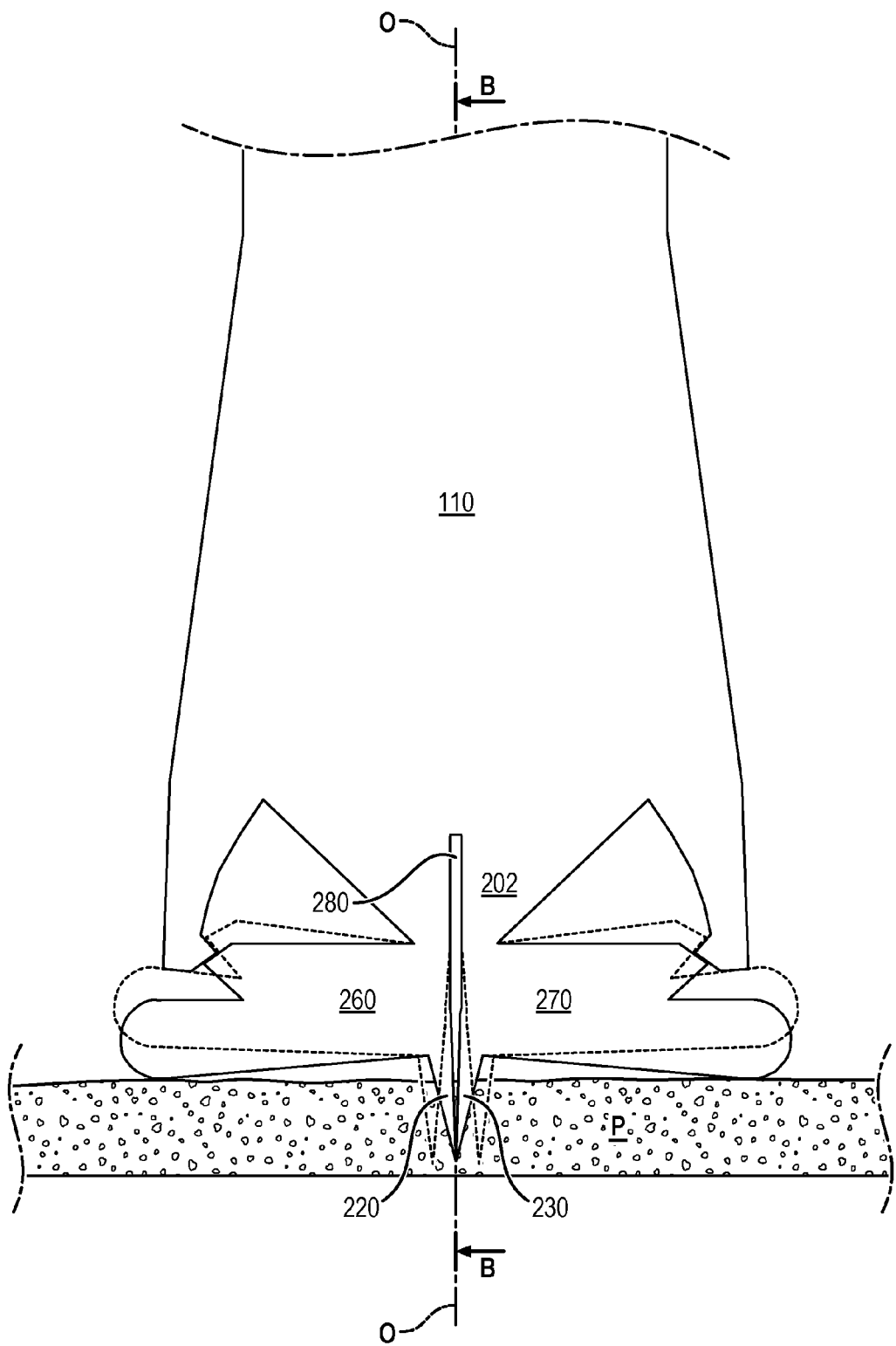

The reservoir 280 of the device must, in the first place, be filled with product suited to its use, for example an allergenic extract, as illustrated in FIG. 4.

In the appended figures, the product is systematically labeled 10 and the skin P.

The reservoir 280 can be pre-filled.

Otherwise, the end of the device must be placed in contact with a reserve of product stored in a suitable container to fill the reservoir 280 by capillary action.

The device is then ready to be used.

In this condition, the channel formed between the surfaces 222 and 232 of the two points 220 and 230, is also filled with product by capillary action.

Unlike conventional devices, thanks to the invention, the product 10 is not deposited on the skin P by means of a distributor. The punch 210 of the device is directly soaked in the reserve of product and its conformation allows the product to penetrate by capillary action into the space 280 in the form of a slot, provided within the end of the device.

After having noted the prick zone and taken customary aseptic precautions, the device according to the present invention is brought into contact with the selected zone of the patient, by placing the end of the punch 210, then the surfaces 262 and 272 of the strips 260 and 270, in contact with the skin.

The punch 210 then pricks and penetrates the skin. After sinking the punch 210, by approximately one third for example, the strips 260 and 270 come into contact with the skin. The progressive contact between the surfaces 262 and 272 of the strips 260 and 270 and the resistance of the skin cause the progressive pivoting of the strips 260, 270, and therefore the separation of the points 220, 230 as shown schematically in FIG. 5, to liberate the product 10.

The points 220 and 230 have totally penetrated the skin when the surfaces 262 and 272 of the strips 260 and 270 are completely joined to the skin as illustrated in FIG. 6.

As can be seen in this FIG. 6, the pivoting of the strips 260 and 270 induces separation of the radially inner facing surfaces 222, 232 of the points 220, 230 and of the radially inner facing surfaces 284, 286 delimiting the chamber 280 beyond the hinge. This separation allows liberation of product contained in the chamber 280 and its penetration into the incision formed in the skin as can be seen in FIG. 6 at the moment where the two points 220, 230 separate by pressing of the strips 260, 270 on the skin.

The complementary hooks or lugs 265 and 293, respectively 275 and 295, then prevent the points or needles 220 and 230 from returning to their initial position and thus prevent the liquid 10 from rising by capillary action along the small channel formed between the points 220, 230, in order to properly fill the space created by the separation of the needles 220, 230.

In working position, the distance separating the end of the points 220 and 230 is typically comprised between 0.2 and 3 mm.

FIG. 7 shows a microscopic drop of product thus distributed into the upper portion of the epidermis after using the device according the present invention.

The remainder of the diagnostic protocol (observation time and references for diagnostic purposes) is conventional.

It will be observed that the structure of the device according to the invention allows optimizing the comfort of the patient, because in the event of a pressure that is slightly too strong, the sufficiently large abutment formed by the surfaces 262 and 272 of the strips allows the patient to be prevented from bleeding. Moreover, this same abutment allows the operator the possibility of a slightly higher pressure in order to avoid false negatives, which allows greater reliability.

Moreover, the injection of the product 10 by the opening of the points 220, 230, once these points are inserted into the skin P, allows better penetration of the product within the epidermis than means known to the prior art requiring pricking through a drop previously deposited on the skin.

The system for separating the two points 220, 230 during use, followed by holding in the separated position thanks to the complementary hooks 265 and 293, respectively 275 and 295, during the removal of the device, allows the certain entry of a sufficiently large microscopic drop of an allergenic extract 10 within the epidermis and therefore reducing the risk of false negatives.

The device according to the present invention offers numerous advantages relative to the devices of the prior art.

It has the following advantages in particular:

it offers total safety for patients, on the one hand, by the absence of risks of contamination between different patients, due to the fact that thanks to the invention it is no longer need or risk placing a pipette or product distributor in contact with the skin of the patient to be tested to deposit a drop of product to be injected (which pipette is then returned to the bottle constituting a product reserve to be reused for the following patients) because according to the invention the device can be pre-filled, in its reservoir 280, with the optimal quantity of product, before being brought into contact with the skin, and on the other hand, due to a guaranteed incision to the optimal depth and only to this depth. Once the surfaces 262, 272 are completely joined to the skin, the device according to the invention guarantees in fact that the points 220 and 230 are integrally inserted into the skin. But these surfaces 262, 272 also guarantee that the points 220 and 230 do not penetrate more deeply into the tissues of the patient.

it allows guaranteeing a perfect reproducibility of penetration of product.

it allows optimizing the consumption of the quantity of product necessary for the diagnosis. The invention allows in particular accurate dosing of the product 10 placed in the reservoir 280 depending on the dose required. The invention thus allows a considerable reduction in the quantity of product used compared to the prior art, which required a greatly oversized drop of product to be placed on the skin compared to the quantity required to be injected.

Typically, the conventional prick test technique includes the deposit of a drop of approximately 50 microliters of extract on the forearm of the patients. Only a tiny part of product is useful in triggering the cutaneous reaction, and it is possible to eliminate the surplus for the patient's comfort. The volume introduced into the device according to the invention is typically approximately 0.2 microliters, or approximately 250 times smaller.

it allows a completely reliable method.

it allows speeding the rapidity of the test sequence.

The conventional technique requires the deposit of a drop of product on the skin, for example on the forearm, for each of the extracts tested, generally on the order of fifteen extracts, before the incision itself is carried out. The device according to the invention requires a simple "presoak" of the end of the device in a solution of allergenic extract with no deposit prior to the incision, which simplifies and shortens the session.

it allows the patient great comfort. Thanks to the invention in particular, there is no longer any obligation to remain in an uncomfortable position during the development of the tests. The conventional technique of an allergic test in fact includes the deposit of a drop on the skin, for example the forearm, of the patients prior to the incision, which requires the patients to hold their forearms, inside upward, in order to prevent the extract from running off. This position is not always comfortable or easy to hold, in particular with young children. The device according to the invention not including a step of depositing the extract, retaining this position is not necessary.

The device according to the present invention can be made of any appropriate material, of metal for example, particularly of stainless steel, or of plastic.

Of course the present invention is not limited to the embodiment which has just been described, but extends to any variant embodiment according to its spirit.

A use of the device according to the present invention for allergic diagnostics was previously described.

The invention is however not limited to this particular application. It can be used in any application requiring cutaneous injection, for example for the injection of a vaccination, by consequently adjusting the length H of the points 220 and 230.

Moreover, a device comprising two points 220 and 230, diametrically opposite relative to the plane BB, was previously described.

Within the scope of the invention, the device can however comprise a greater number of points than two, each associated with an urging means conforming to the strips 260, 270 evenly distributed around the axis O-O.

The variant embodiments according to the invention illustrated in FIGS. 8 and 9 will now be described.

In these FIGS. 8 and 9, elements similar to those described in FIGS. 1 to 7 bear identical numerical labels.

The variant embodiment illustrated in FIG. 8 is essentially distinguished from the embodiment illustrated in FIGS. 1 to 7 by the following dispositions:

the hinge zones 261, 271 are thinner and more rounded, the chamber 280 forming a product reservoir, made at the end of the slot 282, consists of a cavity that is widened compared to the slot, i.e. having a dimension perpendicular to the plane B-B greater than the width of the slot 282 considered perpendicular to this plane B-B, the orientation of the hooks 265, 275 and 293, 295 is inverted, i.e. according to FIG. 8 the hook structures 265 and 275 formed on the strips 260, 270 are oriented to radially inward direction and conversely the hook structure 293 and 295 formed on the arms 292, 294 are oriented to radially outward direction, the axially inner faces 264, 274 of the strips 260, 270 have steps 269, 279 located facing the ends of the arms 292, 294 intended to serve as abutments to the arms 292, 294, limiting the risk of bending of these arms 292, 294 by moving closer to the axis O-O.

The variant embodiment illustrated in FIG. 9 is essentially distinguished from the embodiment illustrated in FIGS. 1 to 7 by the following dispositions:

the arms 292 and 294 have a greater width, so that the arms 292 and 294 shown in FIG. 9 constitute a stronger abutment than the arms shown in FIGS. 1 to 8, and allow limiting the amplitude of deformation of the strips 260, 270 in the event of a strong pressure, the hooks 265/293 and 275/295 serving to hold the cutting points 220, 230 in the open position are moved away from the cutting points so as to preserve better stiffness of the cutting assembly. This disposition also allows amplifying the sound signal generated when the hooks 265/293 and 275/295 are engaged.

The invention claimed is:

1. A cutting device, wherein the cutting device comprises:
a manual gripping element and
a cutting assembly located on one end of the manual gripping element and comprising a punch, split into at least two cutting points,
one at least of at least two cutting points is hinged at a movable point on the manual gripping element in order to be movable between a resting and cutting position wherein the at least two cutting points are adjacent and a working and injection position wherein the at least two cutting points are separated and that the device comprises urging means suited for moving each movable point of the at least two cutting points into the working and injection position, when these urging means come to bear on the skin.

2. The cutting device according to claim 1, wherein the punch is split into the at least two cutting points, each hinged with rotation on the manual gripping element in order to be movable between the adjacent resting and cutting position and a separated working and injection position.

3. The cutting device according to claim 1, wherein each of the at least two cutting points hinged for being movable is connected to the manual gripping element by a hinge zone forming a single piece.

4. The cutting device according to claim 1, wherein the urging means comprise a strip associated respectively with each of the at least two cutting points, which extends perpendicular to a longitudinal axis of the at least two cutting points and which carries a respective of the at least two cutting points, axially external surfaces of the strips forming, at rest, a concave dihedral.

5. The cutting device according to claim 1, wherein the cutting device includes a chamber forming a reserve of product to be injected.

6. The cutting device according to claim 5, wherein the chamber is formed from a slot formed in an end of the cutting assembly and which continues into the punch to individualize the at least two cutting points.

7. The cutting device according to claim 5, wherein the chamber forming a reserve of product consists of a widened cavity formed at the end of a slot made in an end of the cutting assembly and which continues into the punch to individualize the at least two cutting points.

8. The cutting device according to claim 1, wherein the cutting device comprises means for locking the at least two cutting points into the working and injection position.

9. The cutting device according to claim 8, wherein the locking means comprise complementary hooks on the urging means and on arms provided on the end of the manual gripping element.

10. The cutting device according to claim 8, wherein the locking means are located away from the at least two cutting points so as to preserve a stiffness of the cutting assembly and induce a sound signal when the locking means are engaged.

11. The cutting device according to claim 1, wherein the at least two cutting points have a height comprised between 0.5 and 5 mm.

12. The cutting device according to claim 1, wherein the cutting device has a longitudinal axis and two symmetry planes.

13. The cutting device according to claim 1, wherein the cutting device comprises means suited for limiting a movement amplitude of the urging means.

14. The cutting device according to claim 13, wherein the means suited for limiting the movement amplitude of the urging means are formed by arms linked to the manual gripping element and located facing the urging means to serve as an abutment for them.

* * * * *